United States Patent [19]

Leuschner

[11] Patent Number: 5,858,998
[45] Date of Patent: Jan. 12, 1999

[54] BUDESONIDE ALONE OR IN COMBINATION WITH URSODEOXYCHOLIC ACID IN THE THERAPY OF CHOLESTATIC LIVER DISEASES

[75] Inventor: Maria Leuschner, Frankfurt, Germany

[73] Assignee: Dr. Falk Pharma GmbH, Freiburg, Germany

[21] Appl. No.: 940,211

[22] Filed: Sep. 30, 1997

[51] Int. Cl.[6] ................................................. A61K 31/56
[52] U.S. Cl. ............................................................ 514/171
[58] Field of Search ............................................ 514/171

[56] References Cited

U.S. PATENT DOCUMENTS

| | | | |
|---|---|---|---|
| 3,929,768 | 12/1975 | Brattsand et al. | 514/171 |
| 4,917,898 | 4/1990 | Angelico et al. | 424/452 |
| 5,079,240 | 1/1992 | Hofmann | 514/182 |
| 5,234,697 | 8/1993 | Sipos | 424/490 |
| 5,262,172 | 11/1993 | Sipos | 424/490 |
| 5,300,300 | 4/1994 | Egidio et al. | 424/456 |
| 5,352,460 | 10/1994 | Sipos | 424/490 |
| 5,405,621 | 4/1995 | Sipos | 424/490 |
| 5,643,602 | 7/1997 | Ulmius | 424/462 |
| 5,739,161 | 4/1998 | Ueno | 514/530 |

FOREIGN PATENT DOCUMENTS

| | | | |
|---|---|---|---|
| 0508312 | 10/1992 | European Pat. Off. | A61K 31/575 |
| 0509335 | 10/1992 | European Pat. Off. | A61K 31/575 |
| 0510404 | 10/1992 | European Pat. Off. | A61K 31/575 |

OTHER PUBLICATIONS

Abstract of European Patent Application No. 269516 (Poupon), published Jun. 1, 1988, from Derwent Information, Ltd., 1 page, (1995).

Abstract of Japanese Patent Application No. 61158995 (Shironaga), published Jul. 18, 1986, from ACS, 1 pg., (1995).

Abstract of Japanese Patent Application No. 04235918 (Katagiri), published on Aug. 25, 1992, from ACS, 1 pg., (1995).

"Wichtige Neuerungen bei Hepatitiden und Cholestatischen Lebererkrankungen", *Aktuelle Wissenschaft fur Klinik und Praxis,* Satellitensymposium Aktuelle Hepatologie—Diagnostische und Therapeutische Fortschritte 1997, p. 3, (Apr. 1997).

Atkinson, J., et al., "Human Myofibroblastic Ito–Cells (MFI) Receive Growth Signals from Collagen VI (CVI)", *Falk Symposium 87,* Poster 301, 1 pg., (1995).

Bode, J.C., "Klinik und Therapie alkoholischer Leberschaden", *from : Handbuch Alkohol Alkoholismus Alkoholbedingte Organschaden,* Johan Ambrosius Barth, publ., Leipzig, 237–259 (Ch. 11), (1995).

Danielsson, A., et al., "Oral Budenoside for Treatment of Autoimmune Chronic Active Hepatitis", *Aliment Pharmacol Ther,* 8, 585–590, (1994).

Heathcote, E.J., et al., "Combined Analysis of French, American, and Canadian Randomized Controlled Trials of Ursodeoxycholic Acid Therapy in Primary Biliary Cirrhosis", *Gastroenterology,* 108 (supplement), p. A 1082, (Apr. 1995).

Kaplan, M.M., "Medical Approaches to Primary Sclerosing Cholangitis", *Seminars in Liver Disease,* 11, 56–63, (1991).

Leuschner, U., "Gallensauren zur Therapie von Lebererkrankungen", *Internist,* 35, 1147–1155, (1994).

Leuschner, U., et al., "Effects of Ursodeoxycholic Acid After 4 to 12 Years of Therapy in Early and Late Stages of Primary Biliary Cirrhosis", *Journal of Hepatology,* 21, 624–633, (1994).

Leuschner, U., et al., "Ursodeoxycholic Acid in Combination with Prednisolone or Budenoside in the Therapy of Primary Biliary Cirrhosis", *Proceedings of the Falk Symposium No. 93, Bile Acids in Hepatobiliary Diseases: Basic Research and Clinical Application (Oct. 1996 Meeting),* ed. G. Paumgartner et al., Kluwar Academic Publishers, Netherlands, 299–302, (1997).

Leuschner, U., et al., "Ursodeoxycholic Acid in Primary Biliary Cirrhosis: Results of a Controlled Double–Blind Trial", *Gastroenterology,* 97, 1268–1274, (1989).

Mitchison, H.C., et al., "A Controlled Trial of Prednisolone Treatment in Primary Biliary Cirrhosis: Three Year Results", *Journal of Hepatology,* 15, 336–344, (1992).

Mitchison, H.C., et al., "A Pilot, Double–Blind, Controlled 1–Year Trial of Prednisolone Treatment in Primary Biliary Cirrhosis: Hepatic Improvement but Greater Bone Loss", *Hepatology,* 10, 420–429, (1989).

Morgan, T.R., "Treatment of Alcoholic Hepatitis", *Seminars in Liver Disease,* 13, 384–394, (1993).

Neuman, M.G., et al., "Effect of Tauroursodeoxycholic and Ursodeoxycholic Acid on Ethanol–induced Cell Injuries in the Human Hep G2 Cell Line", *Gastroenterology,* 109, 555–563, (1995).

Nolan, J.P., "Intestinal Endotoxins as Mediators of Hepatic Injury—An Idea Whose Time Has Come Again", *Hepatology,* 10, 887–891, (1989).

Paumgartner, G., et al., "Biliary Liver Diseases: Diagnosis, Natural Course and Therapy", *from : Falk Symposium 87, Acute and Chronic Liver Diseases,* ed. R. Schmid et al., Kluwar Academic Publishers, Netherlands, 96–106 (Ch. 8), 1996.

Poupon, R.E., et al., "A Multicenter, Controlled Trial of Ursodiol for the Treatment of Primary Biliary Cirrhosis", *N. Eng. J. Med.,* 324, 1548–1554, (1991).

(List continued on next page.)

*Primary Examiner*—Raymond Henley, III
*Attorney, Agent, or Firm*—Schwegman, Lundberg, Woessner, and Kluth, P.A.

[57] ABSTRACT

According to the invention it was unexpectedly found that budesonide can be used for the treatment of cholestatic liver diseases such as PBC, PSC and AC. In particular budesonide is highly effective when administered together with ursodeoxycholic acid.

10 Claims, No Drawings

OTHER PUBLICATIONS

Poupon, R.E., et al., "Ursodiol for the Long–term Treatment of Primary Biliary Cirrhosis", *New England Journal of Medicine,* 330, 1342–1347, (May 12, 1994).

Rasenack, J., et al., "Primar Biliare Zirrhose, Primar Sklerosierende Cholangitis und Syndrome mit Schwund der Gallengange", *from : Hepatologie,* eds. W. Gerok and H. Blum, Urban & Schwarzenberg, publ., Munich, 426–439 (Ch. 22), (1995).

Schonfeld, J.V., et al., "Primar Biliare Zirrhose (PBS)", *from : Praktische Gastroenterologie,* ed. P. Layer et al., Urban & Schwarzenberg, publ., Munich, 396–399 and 452–457, (1996).

Schwarzenberg, S.J., et al., "Ursodeoxycholic Acid Modifies Gut–Derived Endotoxemia in Neonatal Rats", *Pediatric Research,* 35, 214–217, (1994).

Simko, V., et al., "Ursodeoxycholic Therapy in Chronic Liver Disease: A Meta–Analysis in Primary Biliary Cirrhosis and in Chronic Hepatitis", *American Journal of Gastroenterology,* 89, 392–398, (1994).

Sonnenborn, U., et al., "Beziehungen zwischen Wirtsorganismus und Darmflora", S. 38–39, (1991).

Stiehl, A., et al., "Medical Treatment of Primary Sclerosing Cholangitis: On the of Ursodeoxycholic Acid", *Proceedings of the Falk Symposium No. 93, Bile Acids in Hepatobiliary Diseases: Basic Research and Clinical Application* (*Oct. 1996 Meeting*), ed. G. Paumgartner et al., Kluwar Academic Publishers, Netherlands, 306–314, (1997).

Hoffman, J.C., et al., "Detection of a Soluble Form of the Human Adhesion Receptor Lymphocyte Function–Associated Antigen–3 (LFA–3) in Patients With Chronic Liver Disease", *Journal of Hepatology,* 25, 465–473, (1996).

Larusso, N., "Search for Medical Treatment for Primary Biliary Cirrhosis", *Lancet,* 350, 1046, (1997).

Rambusch, E.G., et al., "Immunsuppressive Therapie der Autoimmunen Lebererkrankungen", *Internist,* 38, 574–581, (1997).

BUDESONIDE ALONE OR IN COMBINATION WITH URSODEOXYCHOLIC ACID IN THE THERAPY OF CHOLESTATIC LIVER DISEASES

FIELD OF THE INVENTION

The present invention relates to the use of budesonide either alone or in combination with ursodeoxycholic acid for the treatment of cholestatic liver diseases, in particular of primary biliary cirrhosis, primary sclerosing cholangitis and autoimmune cholangitis.

BACKGROUND OF THE INVENTION

Pharmaceutical compositions comprising immuno suppressives, e.g. corticosteroids such as prednisolone or budesonide are well known for the treatment of hepatic diseases (Danielsson et al., Aliment. Pharmacol. Ther., 1994, 8, 585–590). Different in many aspects from other hepatic diseases, however, are, cholestatic diseases such as primary biliary cirrhosis (PBC), primary sclerosing cholangitis (PSC) and autoimmune cholangitis (AC). It was the general belief in the art that the therapy with such immuno suppressives is not promising for the treatment of cholestatic diseases.

In particular, there were controlled clinical investigations whether prednisolone can be used for the treatment of PBC (Mitchison et al., Hepatology, 1989, 4, 420–429; Mitchison et al., Journal of Hepatology, 1992, 15, 336–344), however, the therapy with prednisolone is controversially discussed. The activity of prednisolone is not without doubt and, furthermore, severe side effects were observed. For this reason, up to now a therapy of PBC, PSC and AC with glucocorticoids was not considered being helpful (Paumgartner & Beuers, In: Falk Symposium 87, Acute and chronic liver diseases, 1996, 96–106; Rasenack and Gerok in Hepatologie (Ed. Gerok & Blum), 1995, page 435 and 439; Praktische Gastroenterologie, (Ed. Layer et al.), 1996, 397–398).

Therefore, for the treatment of cholestatic liver diseases there was up to now no alternative to a therapy with ursodeoxycholic acid which may not completely heal the disease but impressively alleviates the symptoms of the disease and improves the laboratory values (The new England Journal of Medicine, 1991, 1548; Seminars in Liver Disease, Volume 11, No. 1, 1991, 56; Gastroenterology 97, 1989, 1268; Internist, 35, 1994, 1147 and Journal of Hepatology, 21, 1994, 624–633).

Despite the fact that treatment with ursodeoxycholic acid alleviates the symptoms of the cholestatic liver diseases to some degree, there is still need in the art for further pharmaceutical compositions and methods for improving the treatment of cholestatic liver diseases, in particular of primary biliary cirrhosis (PBC), primary sclerosing cholangitis (PSC) and autoimmune cholangitis (AC).

SUMMARY OF THE INVENTION

An object of the present invention is therefore to provide new methods and medicaments for treating cholestatic liver diseases such as PBC, PSC and AC. Another object of the present invention is to provide a method for enhancing the activity of ursodeoxycholic acid in the treatment of cholestatic liver diseases such as PBC, PSC and AC.

Other objects of the present invention are apparent for a skilled person on the basis of the following detailed description.

These objects are achieved on the basis of the unexpected finding that the glucocorticoid budesonide,

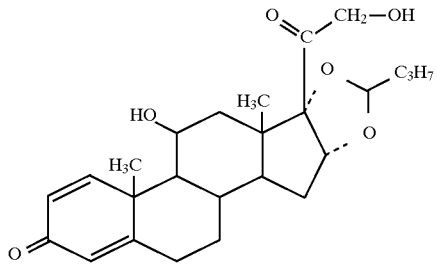

which up to the findings of the present inventors was believed to be useful only for the treatment of non cholestatic liver diseases, is also useful in the treatment of cholestatic liver diseases such as PBC, PSC and AC. It was furthermore unexpectedly found that budesonide when administered together or timely shifted with ursodeoxycholic acid improves the activity of ursodeoxycholic acid in the treatment of cholestatic liver diseases such as PBC, PSC and AC.

Therefore, the present invention provides the use of budesonide for the treatment of cholestatic liver diseases, in particular of primary biliary cirrhosis, primary sclerosing cholangitis and autoimmune cholangitis. Furthermore, the present invention provides the use of a combination of budesonide and ursodeoxycholic acid for the treatment of cholestatic liver diseases, in particular for the treatment of primary biliary cirrhosis, of primary sclerosing cholangitis and of autoimmune cholangitis.

The present invention furthermore provides a pharmaceutical composition comprising budesonide for the treatment of cholestatic liver diseases, in particular of primary biliary cirrhosis, primary sclerosing cholangitis and autoimmune cholangitis.

The present invention furthermore provides a pharmaceutical pack comprising a pharmaceutical composition comprising budesonide as active agent and a pharmaceutical composition comprising ursodeoxycholic acid as pharmaceutically active agent for joined or timely shifted administration, in particular for the treatment of cholestatic liver diseases such as primary biliary cirrhosis, primary sclerosing cholangitis and autoimmune cholangitis.

The present invention furthermore provides a pharmaceutical composition comprising budesonide and ursodeoxycholic acid, in particular for the treatment of cholestatic liver diseases such as primary biliary cirrhosis, primary sclerosing cholangitis and autoimmune cholangitis.

DETAILED DESCRIPTION OF THE INVENTION

Budesonide is a potent corticosteroid with a high topical activity and low systemic availability in therapeutic doses. Affinity to the glucocorticoid receptor is about 15 times higher for budesonide compared to prednisolone. Budesonide is well absorbed from the intestine, has an extensive first pass metabolism and 80 to 90% of an orally given dose is metabolized in the liver during the first liver pass in healthy subjects. The systemic bioavailability is about 10%. Because of these properties budesonide belongs to the steroids having very low side effects, however, the very high first pass metabolism and the low systemic bioavailability of budesonide apparently exclude a successful treatment of cholestatic liver diseases. It was therefore surprising that budesonide has an activity in the treatment of cholestatic liver diseases.

According to the present invention, it is possible to treat cholestatic liver diseases such as PBC, PSC and AC with budesonide, i.e. a budesonide containing pharmaceutical composition. Such a treatment alleviates the symptoms of cholestatic liver diseases. Budesonide can be formulated to a pharmaceutical composition for the treatment of mammals, preferably humans in a per se known manner. In the pharmaceutical composition budesonide usually is in admixture with a pharmaceutically acceptable organic or inorganic carrier which is suitable for the enteral or parenteral application.

Oral preparations of the pharmaceutical compositions of the invention such as by tablets, capsules, powders, liquids such as suspensions, solutions or emulsions or as a syrup are preferred. When budesonide is formulated as a tablet, usual carriers and excipients such as lactose, microcrystalline cellulose, starch and anhydrous silica, lubricants such as hydrated castor oil, magnesium stearate, sodium lauryl sulfate and talc as well as binders such as starch, glucose, gum arabicum and mannitol are used. If the compositions of the invention are in a liquid state, usual liquid carriers can be used. Preferred is a formulation of the pharmaceutical compositions of the invention as injection or infusion or as a suppository, as is known in the prior art and described in well known standard text books such as Remington: The Science and Practice of Pharmacy, 19th ed.; Mack Publishing Company, Easton, Pa., 1995.

In a particularly preferred embodiment of the present invention, the budesonide containing pharmaceutical compositions are formulated with the excipients corn starch, lactose, aerosil, polyvinylpyrrolidone and magnesium stearate to tablets. In a further particularly preferred embodiment of the present invention, the budesonide containing pharmaceutical compositions are formulated with the excipients corn starch, lactose, magnesium stearate and aerosil to capsules.

The budesonide containing compositions of the present invention can furthermore be formulated as sustained release preparations, as is known in the art, e.g. from Remington: The Science and Practice of Pharmacy, 19th ed.; Mack Publishing Company, Easton, Pa., 1995.

The daily dose of budesonide is about 0.5 mg to 100 mg per day depending on the severity of the disease, the stage of the disease, further diseases of the patient, the administration route and further parameters which are known to the skilled person. Preferred are daily doses of 1 mg to 50 mg and particularly preferred are daily doses of 5 mg to 20 mg. The daily doses can be administered at one time per day or divided over the day, for example three times a day. Correspondingly, the budesonide containing pharmaceutical compositions of the invention comprise preferably 0.5 to 20 mg, particularly preferred 1 mg to 5 mg budesonide per unit dosage form.

According to the invention it was furthermore unexpectedly found that budesonide can improve the therapeutic effects of ursodeoxycholic acid in the treatment of cholestatic liver diseases such as PBC, PSC and AC if budesonide is administered together or timely shifted with the ursodeoxycholic acid. These unexpected improvements of the activity of ursodeoxycholic acid by joined or timely shifted administration of budesonide was found for the first time by the present inventors and they published part of their results on Apr. 5, 1997 in the journal "Aktuelle Wissenschaft für Klinik und Praxis", Satellitensymposium, "Aktuelle Hepatologie—Diagnostische und Therapeutische Fortschritte 1997", page 3, which is hereby incorporated by reference. The present inventors furthermore published parts of their results in U. Leuschner et al., Ursodeoxycholic acid in combination with prednisolone or budesonide in the therapy of primary biliary cirrhosis, In: Bile acids in Hepatobiliary Diseases: Basic Research and Clinical Application. S. 299–302, Kluwer Academic Publishers, Dordrecht, 1997, which is hereby incorporated by reference. In a particularly preferred embodiment of the present invention, therefore, budesonide is not administered to a patient in need thereof as the sole active agent, but rather is administered together or timely shifted with the well known pharmaceutically active agent ursodeoxycholic acid.

While it is possible to administer a pharmaceutical composition comprising both ursodeoxycholic acid and budesonide, it is preferred to administer two pharmaceutical compositions, one comprising ursodeoxycholic acid as active ingredient and the other comprising budesonide as active ingredient jointly or timely shifted. By the expression "jointly or timely shifted" administration of the budesonide containing and the ursodeoxycholic acid containing pharmaceutical composition for the purpose of the present invention it is understood that both pharmaceutical compositions are administered to a patient in need thereof in such a time interval that the budesonide containing pharmaceutical composition suitably enhances the activity of the ursodeoxycholic acid containing pharmaceutical composition. In general, both pharmaceutical compositions are administered within one day, however, in some cases it may also be possible to enhance the activity of ursodeoxycholic acid, if the budesonide containing pharmaceutical composition and the ursodeoxycholic acid containing pharmaceutical composition are administered in an interval of more than 24 hours.

More details of the most preferred administration route for the budesonide containing pharmaceutical composition and the ursodeoxycholic acid containing pharmaceutical composition are discussed below.

In the ursodeoxycholic acid containing pharmaceutical compositions of the present invention ursodeoxycholic acid usually is in admixture with a pharmaceutically acceptable organic or inorganic carrier which is suitable for enteral or parenteral application. Oral preparations of the ursodeoxycholic acid containing pharmaceutical compositions of the invention such as by tablets, capsules, powders, liquids such as suspensions, solutions or emulsions or as a syrup are preferred. When ursodeoxycholic acid is formulated as a tablet usual carriers and excipients such as sodium citrate, lactose, microcrystalline cellulose and starch, lubricants such as anhydrous silica, hydrated castor oil, magnesium stearate, sodium lauryl sulfate and talc as well as binders such as starch, glucose, lactose gum arabicum, mannitol, magnesium trisilicate and talc are used. If the ursodeoxycholic acid containing compositions of the invention are in a liquid state usual liquid carriers can be used. Preferred is a formulation of the ursodeoxycholic acid containing pharmaceutical compositions of the invention as injection or infusion, as is known in the prior art and described in well known standard text books such as Remington: The Science and Practice of Pharmacy, 19th ed.; Mack Publishing Company, Easton, Pa., 1995.

In a particularly preferred embodiment of the present invention the ursodeoxycholic acid containing pharmaceutical compositions are formulated with the excipients corn starch, aerosil, magnesium stearate, lactose and polyvinylpyrrolidone to tablets. In a further particularly preferred embodiment of the present invention the ursodeoxycholic acid containing pharmaceutical compositions are formulated with the excipients corn starch, aerosil and magnesium stearate to capsules.

The ursodeoxycholic acid containing compositions of the present invention can furthermore be formulated as sustained release preparations, as is known in the art e.g. in Remington: The Science and Practice of Pharmacy, 19th ed.; Mack Publishing Company, Easton, Pa., 1995.

The daily dose of ursodeoxycholic acid is preferably about 0.5 mg/kg body weight to 100 mg/kg body weight ursodeoxycholic acid per day, more preferably 1 mg/kg body weight to 50 mg/kg body weight per day and particularly preferred 5 mg/kg body weight to 20 mg/kg body weight per day, depending on the severity of the disease, the stage of the disease, further diseases of the patient, the administration route and further parameters which are known to the skilled person. The daily doses can be administered at one dose a day or divided over several doses per day. Correspondingly, the ursodeoxycholic acid containing pharmaceutical compositions of the invention contain preferably 7 mg to 1,400 mg, more preferred 100 mg to 1000 mg ursodeoxycholic acid per unit dosage form.

Of course, it is possible to administer the budesonide containing pharmaceutical composition and the ursodeoxycholic acid containing pharmaceutical composition in different dosage forms, for example administering tablets containing budesonide and an infusion or an injection containing ursodeoxycholic acid or administering the budesonide in form of suppositories and the ursodeoxycholic acid in form of a tablet or a capsule. Preferably both pharmaceutical compositions are administered in the form of tablets or capsules.

Both, budesonide containing pharmaceutical compositions and ursodeoxycholic acid containing pharmaceutical compositions are already known and in use for the treatment of some diseases as discussed above. According to the invention, it is possible to administer the known pharmaceutical compositions containing budesonide alone or together or timely shifted with the known pharmaceutical compositions containing ursodeoxycholic acid.

If budesonide and ursodeoxycholic acid are formulated in one pharmaceutical composition, the same excipients and carriers can be used as discussed above in connection with the budesonide containing pharmaceutical compositions and the ursodeoxycholic acid containing pharmaceutical compositions. A pharmaceutical composition containing both budesonide and ursodeoxycholic acid should contain both pharmaceutically active agents in such a concentration that the above mentioned daily doses of both active agents are achieved. The formulation of such pharmaceutical compositions is well known in the prior art and described in standard text books of the field such as Remington: The Science and Practice of Pharmacy, 19th ed.; Mack Publishing Company, Easton, Pa., 1995.

The examples reported below have to be considered only as a further illustration and not as a limitation of the invention.

Formulation example 1: budesonide containing tablets (5 mg)

| Budesonide | 50 g |
|---|---|
| Corn starch | 450 g |
| Lactose | 450 g |
| Aerosil | 50 g | are mixed and wetted with

| Polyvinylpyrrolidone | 100 g |
|---|---| dissolved in 500 ml ethanol (70%).

The moist mass is passed through a 1 mm-sieve and dried. After renewed sieving of the dried mass

| Magnesium stearate | 30 g |
|---|---| are added.

The mixture is pressed into tablets of 120 mg.

Formulation example 2: budesonide containing capsules (3 mg)

| Budesonide | 30 g |
|---|---|
| Corn starch | 300 g |
| Lactose | 200 g |
| Magnesium stearate | 30 g |
| Aerosil | 20 g | are mixed and are filled into hardgelatine-capsules. The filling weight is 58 mg.

Formulation example 3: budesonide containing injection (3 mg/ml)

| | Budesonide | 3 g |
|---|---|---|
| is dissolved in | | |
| | Lecithin (USP 23) | 60 g |

The solution is instilled into 1000 ml of water (pH 3,5, citrate buffer, 50 mM) under strong shearing with an Ultraturrax. The resulting solution is filled into 1 ml phiols and sterilized for 20 min at 121° C.

Formulation example 4: budesonide containing suppositories (10 mg)

| Budesonide (micronized) | 10 g |
|---|---| is suspended in

| Hard fat | 2000 g |
|---|---| which is melted to approximately 45° C. and is then poured into 2 g suppository molds. After cooling down the suppositories are taken out.

Formulation example 5: ursodeoxycholic acid containing tablets (500 mg)

| Ursodeoxycholic acid, microcrystalline | 500 g |
|---|---|
| Corn starch | 200 g |
| Lactose | 115 g |
| Aerosil | 5 g | are mixed and wetted with

| Polyvinylpyrrolidone | 15 g |
|---|---| dissolved in 150 ml ethanol (70% (w/w)).

The moist mass is passed through a 1 mm sieve and dried. After renewed sieving of the dried mass

| | |
|---|---|
| Magnesium stearate | 15 g | are added.

The mixture is pressed into tablets of 850 mg.

Formulation example 6: Ursodeoxycholic acid containing capsules (250 mg)

| | |
|---|---|
| Ursodeoxycholic acid, microcrystalline | 250 g |
| Corn starch | 140 g |
| Magnesium stearate | 5 g |
| Aerosil | 5 g | are mixed and are filled into hardgelatine-capsules. The filling weight is 400 mg.

Formulation example 7: Ursodeoxycholic acid containing injection (20 mg/ml)

| | |
|---|---|
| Sodium hydrogencarbonate | 10 g | are dissolved in 900 ml water for injection.

| | |
|---|---|
| Ursodeoxycholic acid | 20 g | are added. Under slight warming (appr. 45° C.) and stirring, UDCA is dissolved. After cooling to 20° C. the solution is filled up to 1000 ml with water for injection. The solution is filled into 10 ml vials. After sealing the vials are sterilized at 120° C. for 20 min.

For infusion 10 ml of the sterilized solution are mixed with 250 ml of a 5% (w/w) commercially available human albumin solution.

EXPERIMENTAL EXAMPLE 1

A female patient with the diagnosis PBC was treated with 3 * 3 mg budesonide per day over a longer period of time. Prior to the therapy the clinical parameters were determined, and these parameters were followed during the therapy (table 1). As clinical parameters the enzyme activities of GPT (Alanine-Aminotransferase), AP (Alkaline Phosphatase), and LAP (Leucineaminopeptidase) were used. The GPT is an enzyme which has the highest activity in the liver. An increase in the serum activity of this enzyme (normal: up to 22 U/l) points to a damaged liver with a high specificity. An increase in the serum activity of the AP (normal: up to 170 U/l) occurs with all diseases of the liver and the biliary tract, which occur in combination with a cholestatic disease. A further parameter pointing to a cholestatic liver disease is the serum activity of the LAP. An increased value of the enzyme activity in the serum (normal: 11–35 U/l) points to a hepatic-biliary disease with obstructive and nonobstructive cholestasis.

As can be seen from table 1, prior to the treatment with budesonide all serum activities described above of the female patient with indicated PBC were higher than normal.

After treatment for only one month with a daily dose of 3 * 3 mg budesonide all parameters were significantly improved and did not increase again, even after a treatment of 12 months. No side effects were observed during the whole treatment period.

TABLE 1

Serum activity of various liver enzymes [U/1]

| treatment period | GPT [U/1] | AP [U/1] | LAP [U/1] |
|---|---|---|---|
| prior to the treatment | 32 | 187 | 53 |
| after 1 mon. therapy | 9 | — | — |
| after 2 mon. therapy | 10 | — | 29 |
| after 12 mon. therapy | 7 | 117 | 29 |

This clearly shows that cholestatic liver diseases can successfully be treated with budesonide.

I claim:

1. A pharmaceutical pack comprising a pharmaceutical composition comprising budesonide as pharmaceutically active agent and a pharmaceutical composition comprising ursodeoxycholic acid as pharmaceutically active agent for joined or timely shifted administration.

2. A pharmaceutical composition comprising budesonide and ursodeoxycholic acid.

3. A method for treating a cholestatic liver disease comprising administering to a human afflicted with cholestatic liver disease, an amount of budesonide effective to alleviate a symptom of the disease.

4. The method of claim 3 wherein the cholestatic liver disease is primary biliary cirrhosis.

5. The method of claim 3 wherein the cholestatic liver disease is primary sclerosing cholangitis.

6. The method of claim 3 wherein the cholestatic liver disease is autoimmune cholangitis.

7. A method for treating a cholestatic liver disease comprising administering to a human afflicted with cholestatic liver disease a combination of budesonide and ursodeoxycholic acid.

8. The method of claim 7 wherein the cholestatic liver disease is primary biliary cirrhosis.

9. The method of claim 7 wherein the cholestatic liver disease is primary sclerosing cholangitis.

10. The method of claim 7 wherein the cholestatic liver disease is autoimmune cholangitis.

* * * * *